US00PP35021P2

(12) United States Plant Patent
Tuite

(10) Patent No.: US PP35,021 P2
(45) Date of Patent: Mar. 7, 2023

(54) ***GERANIUM* PLANT NAMED 'TUITSKI'**

(50) Latin Name: *Geranium pratense*
Varietal Denomination: TUITSKI

(71) Applicant: GENESIS PLANT MARKETING LTD., Langford (GB)

(72) Inventor: Jonathan Tuite, Westacre (GB)

(73) Assignee: GENESIS PLANT MARKETING LTD., Langford (GB)

( * ) Notice: Subject to any disclaimer, the term of this patent is extended or adjusted under 35 U.S.C. 154(b) by 5 days.

(21) Appl. No.: 17/739,140

(22) Filed: May 8, 2022

Related U.S. Application Data

(60) Provisional application No. 63/188,345, filed on May 13, 2021.

(51) Int. Cl.
*A01H 5/02* (2018.01)
*A01H 6/42* (2018.01)

(52) U.S. Cl.
USPC ..... Plt./324

(58) Field of Classification Search
USPC ..... Plt./263.1, 324
See application file for complete search history.

(56) References Cited

U.S. PATENT DOCUMENTS

PP10,695 P * 11/1998 Nicholson ..... Plt./324

OTHER PUBLICATIONS

Breck's Cataloge. 2022. https://www.brecks.com/product/Double-Geranium-Summer-Skies. 1 pg. (Year: 2022).*

* cited by examiner

*Primary Examiner* — Karen M Redden
(74) *Attorney, Agent, or Firm* — Penny J. Aguirre

(57) ABSTRACT

A new cultivar of *Geranium* plant named 'TUITSKI' that is characterized by its flowers that are deep blue in color, its flowers that are large in size, and its fully double flowers.

2 Drawing Sheets

Botanical classification: *Geranium pratense.*
Varietal denomination: 'TUITSKI'.

BACKGROUND OF THE INVENTION

The present invention relates to a new and distinct cultivar of *Geranium pratense* and will be referred to hereafter by its cultivar name, 'TUITSKI'. 'TUITSKI' represents a new *Geranium*, an herbaceous perennial grown for landscape use.

'TUITSKI' was discovered by the Inventor as a chance seedling outdoors in a perennial border of *Geranium* in Westacre, Norfolk, The United Kingdom in July of 2016. The exact parentage is unknown, however *Geranium pratense* 'Fiore Plena' (not patented, syn. *Geranium pratense* 'Plenum Violaceum') is thought to be a parent based on its charateristics and its proximity in the perennial border.

Asexual propagation of the new cultivar was first accomplished under the direction of the Inventor by division in April of 2017 in Westacre, Norfolk, The United Kingdom. Asexual propagation by division and tissue culture using meristematic tissue has shown that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'TUITSKI' as a new and unique cultivar of *Geranium.*

1. 'TUITSKI' exhibits flowers that are deep blue in color.
2. 'TUITSKI' exhibits flowers that are large in size.
3. 'TUITSKI' exhibits fully double flowers.

The probable parent parent plant, 'Fiore Plena', differs from flowers that are violet blue in color. 'TUITSKI' 'TUITSKI' can be most closely compared to the *Geranium pratense* cultivars 'Summer Skies' (U.S. Plant Pat. No. 10,695) and 'Cloud 9' (not patented). 'Summer Skies' and 'Cloud 9' are both similar to 'TUITSKI' in having double flowers. 'Summer Skies' differs from 'TUITSKI' in having flowers that are violet blue with a hint of white in color. 'Cloud 9' differs from 'TUITSKI' in having flowers that are pale blue in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales that fall within a one-year grace period prior to the filing date. Disclosures include website listings by to disclosures on websites by Thompson and Morgan, The Hardy *Geranium* Nursery, Van Meuwen, Walter Blom Plants B.V., Crocus, RHS Plants, Hortweek, Genesis Plant Marketing Ltd, Suttons, Algera, Dorset Perennials, Waitrose Garden, Penlan Perennials Nursery, Hayloft, RadioTimes Gardening, Jardins Paquette, 4uToday, Hogendoorn, Barnes Nurseries, Pick UK, Plant Estate, Hansu, Clockhouse Nursery, Spaargaren, Cool Plants, Blomqvist, and Beyond the Garden Gates.

BRIEF DESCRIPTION OF THE DRAWINGS

The accompanying color photographs illustrate the overall appearance and distinct characteristics of the new *Geranium.*

The photograph in FIG. 1 was taken of a plant 2 years in age as grown outdoors (photographed in high light indoors) in a 17-cm container in Heeerhugowaard, The Netherlands and provides a side view of 'TUITSKI' in bloom.

Figure 1:
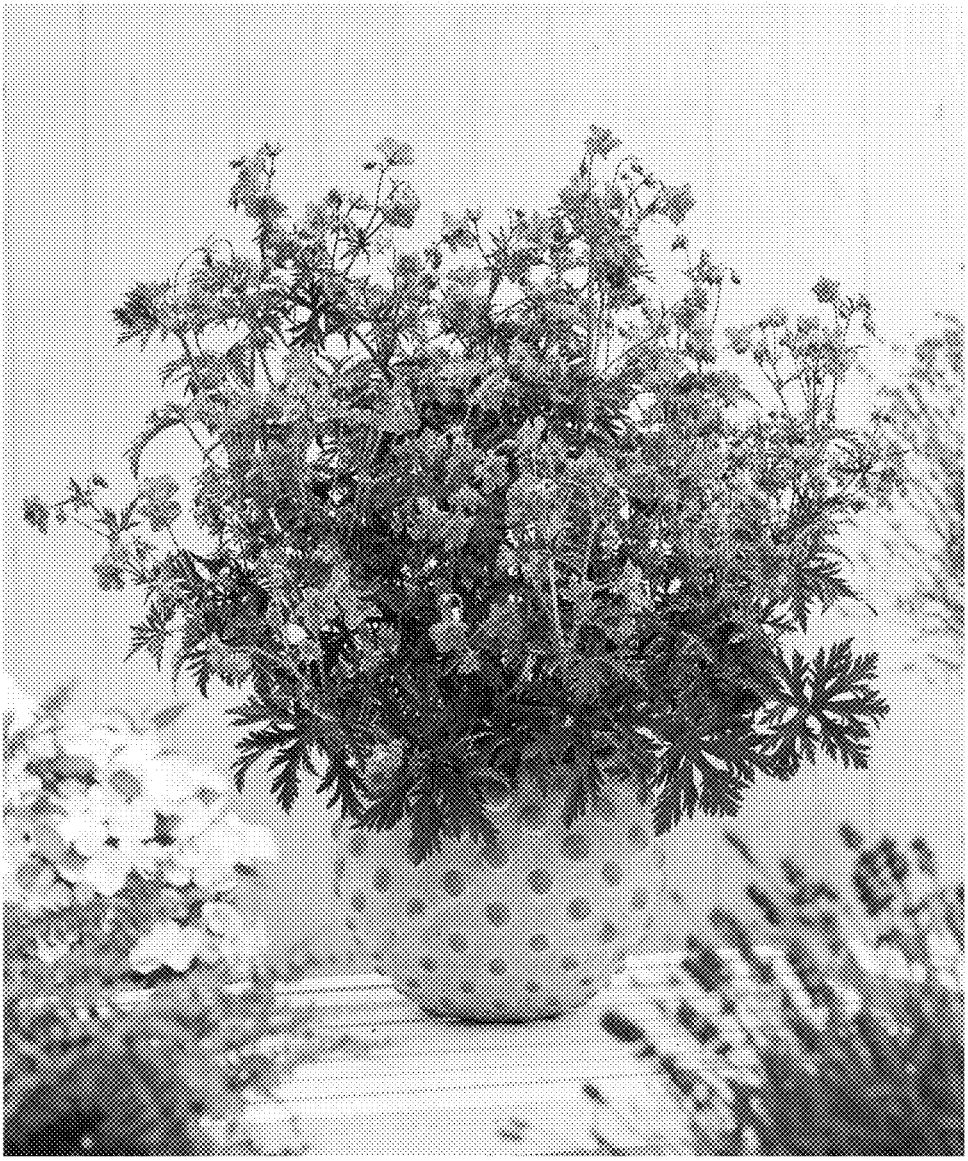
Figure 2:
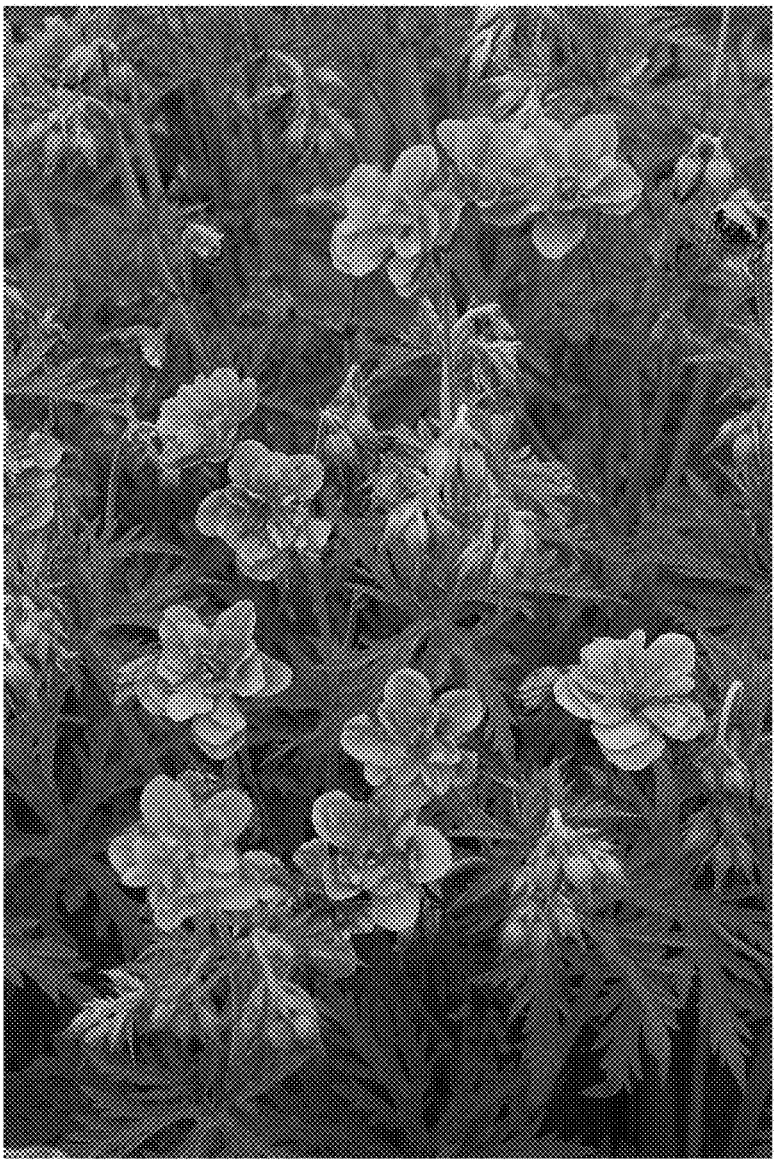

The photograph in FIG. 2 was taken of a plant 2 years in age as grown in a garden in Westacre, Norfolk, The United Kingdom and provides a close-up view of the flowers of 'TUITSKI'.

The colors in the photographs are as close as possible with the photographic and printing technology utilized and the color values cited in the detailed botanical description accurately describe the colors of the new *Geranium.*

DETAILED BOTANICAL DESCRIPTION OF THE PLANT

The following is a detailed description of 1-year-old plants of the new cultivar as grown outdoors in 17-cm containers in Heeerhugowaard, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Spring into summer in The United Kingdom.

*Plant type.*—Herbaceous perennial.

*Plant habit.*—Broadly spreading and upright.

*Height and spread.*—An average of 52 cm in height (soil level to top of foliar plane), 61.4 cm in height (soil level to top of floral plane) and 96.7 cm in width.

*Cold hardiness.*—At least in U.S.D.A. Zones 5 to 9.

*Diseases and pests.*—No susceptibility or resistance to diseases or pests has been observed.

*Root description.*—Non-fibrous, slightly fleshy, 2 mm in diameter, slightly to moderately branched, sparse, smooth and glabrous, 164B in color, shallow to moderately deep.

*Propagation type.*—Division and tissue culture.

*Root development.*—Time required for root initiation is 2 to 3 weeks, time required to produce a young plant from a stage 3 tissue plant into a plug is 6 to 8 weeks, about 36 weeks from propagation to a salable plant.

*Growth rate.*—Vigorous.

Stem description:

*Stem shape.*—Rounded.

*Stem color.*—Young; 144B with distal end 144A, mature; upper surface 183A to 183B, lower surface 144B, internodes 178C and 183A.

*Stem size.*—An average of 48 cm in length and 6 mm in diameter.

*Stem surface.*—Moderately glossy, densely covered with short glandular and slightly sticky hairs, 0.5 mm in length, 156D in color.

*Stem aspect.*—Stems held in an average angle of 37.5° to vertical.

*Internode length.*—An average of 10.6 cm.

*Stem strength.*—Moderately strong.

*Branching habit.*—An average of 11 main basal stems and 6 lateral branches per main stem.

Foliage description:

*Leaf shape.*—Reniform to broadly ovate in outline.

*Leaf division.*—Simple.

*Leaf base.*—Hastate, lobes touching to slightly overlapping.

*Leaf apex.*—Acute.

*Leaf venation.*—Palmate, upper surface 144B, lower surface 147C to 147D.

*Leaf margins.*—Coarsely serrate to laciniate, palmately and deeply cleft with an average of 7 lobes, convergent.

*Leaf attachment.*—Petiolate.

*Leaf arrangement.*—Basal leaves alternate, stem leaves opposite.

*Leaf aspect.*—Average of 90° to the stem.

*Leaf surface.*—Both surfaces pubescent, matte, slightly rugose, densely covered with short hairs, an average of 0.25 mm in length, 156D.

*Leaf color.*—Young upper surface; NN137C, young and mature lower surface; 138B, mature upper surface; 137A.

*Leaf number.*—Average of 12 (6 pairs) per main stem.

*Leaf size.*—Basal leaves; 15 cm in length, 15.3 cm in width, stem leaves; 10.5 cm in length, 12.5 cm in width.

*Petioles.*—Strong, basal leaves; 36.2 cm in length, 3.5 mm in diameter, color; 177B, base 178B, stem leaves; 8.9 cm in length, 2 mm in diameter, color; 176A, surfaces are moderately glossy, densely covered with short hairs, average of 0.4 mm in length, 156D in color.

*Stipules.*—Two leafy stipules are present at the base of every leaf, lanceolate, apex is long and acuminate, base is broadly cuneate, average of 1.1 cm in length, 4 mm in width, color; both surfaces are 164B with main veins 164A.

Flower description:

*Flower type.*—Axillary, solitary or in pairs.

*Flower fragrance.*—None.

*Flower lastingness.*—Average of 7 days on plant, self-cleaning.

*Inflorescence size.*—An average of 6.2 cm in height, 5.4 cm in diameter.

*Flower buds.*—Average of 8 mm in length, 5 mm in diameter, ovate in shape, color; 143C, axially striped 143B, proximal end 178B, surface is matte, densley covered with short glandular hairs, an average of 0.5 mm in length, 156D in color.

*Flower quantity.*—Average of 4 per inflorescence, 800 flowers per plant, 200 buds per plant.

*Flower aspect.*—Outwardly to upright.

*Flower shape.*—Rotate, fully-double, petals free.

*Flower size.*—An average of 2.9 cm in height and diameter, 1.5 cm in length.

*Peduncles.*—Moderately strong, average of 2.7 cm in length, 1 mm in diameter, held in an average angle of 70° to lateral branch, color; 144B, upper side moderately tinged with 197B, moderately glossy, densely covered with somewhat sticky, short glandular hairs; an average of 0.3 mm in length, 156D in color.

*Pedicels*.—Moderately strong, average of 1.6 cm in length, 1 mm in diameter, held in an average angle of 30° to lateral branch, color; 144B, upper side moderately tinged with 183A, moderately glossy, densely covered with somewhat sticky, short glandular hairs; an average of 0.3 mm in length, 156D in color.

*Petal description*.—5, obcordate in shape, an average of 1.5 cm in length and 1.2 cm in width, narrowly cuneate base, margin is entire, apex is obtuse, upper and lower surface is glabrous, slightly velvety in appearance, non-rugose, color; upper and lower surface when opening N88B, changing to N87B at the base, veins 85D, fully open upper surface N88B to N88C, changing to N87C to N87D at the base, fully open lower surface between 86C and N88B to N88C, changing to N87C at the base, both surfaces veins fade to 85C.

*Calyx form*.—Rotate, 8 mm in length, 2.2 cm in diameter.

*Petaloids*.—Rotate, average of 10 per flower, 2 whorls, unfused, lower whorl; narrow obovate in shape, tips obtuse, cuneate base, margins entire and medium undulate, 1.5 cm in length, 9 mm in width, color; when opening upper surface N88B, base N87B, veins 85D, when opening lower surface between N87B and N88B, base N87B, veins 85D, fully open upper surface N88B to N88C, base N87C to N87D, fully open lower surface between 86C and N88B to N88C, base N87C, veins on upper and lower surface when fully open N87B, upper whorl; irregular narrow obovate to irregular oblanceolate in shape, tips irregular acute to irregular obtuse, 1.4 cm in length, 5 mm in width, margins entire and medium to highly undulate, color; when opening upper and lower surface N87A, base N81A, fully open upper and lower surface N87B, tip N88B and occasionally 145A, base N81C, veins on upper and lower surface when fully open 85C, surface both surfaces non-rugose, matte, slightly velvety.

*Sepals*.—Rotate, an average of 5 in 1 whorl, average of 1.3 cm in length and 4.5 mm in width, narrow ovate in shape, margin is entire, mucronate apex, cuneate base, upper surface is glabrous and smooth, moderately glossy, lower surface is densely covered with short glandular hairs; average of 0.3 mm in length, 156D in color, matte, color; when opening upper and lower surface 144B, margined 157A, veined 146A, when fully open upper and lower surface 144B, margined 157A, slightly tinged at the base 178C, veins 146A, slightly tinged at the base 178C.

*Bracts*.—2 placed at the base of each pedicel, lanceolate in shape, average of 5 mm in length, 1.25 mm in width, entire margins, long mucronatte tip, cuneate base, upper surface smooth and glabrous, color; both sides 181B, lower surface and margins moderately covered with somewhat sticky, short glandular hairs average of 0.3 mm in length, 156D in color.

Reproductive organs:

*Gynoecium*.—Pistil; 1, 1 cm in length, stigmas; 5, irregularly curled, 4 mm in length, 6 mm in diameter, 144B in color, style; 4 mm in length, 144B in color, ovary; 143C in color.

*Androecium*.—None present, stamen transformed into petaloids.

*Fruit and seed*.—Fruit; Average of 1,000 per plant, 2.3 cm in length, 6 mm in diameter, color; 143C, base 150B, persistent styles and stigmas 180D, surface is densely covered with somewhat sticky, short glandular hairs, 0.5 mm in length, 156D in color, no seeds detected in the fruit.

It is claimed:

1. A new and distinct cultivar of *Geranium* plant named 'TUITSKI' as herein illustrated and described.

* * * * *